US012611100B2

(12) United States Patent
Sinha et al.

(10) Patent No.: US 12,611,100 B2
(45) Date of Patent: Apr. 28, 2026

(54) AFFERENT PUPIL DEFECT TESTING IN A VR HEADSET

(71) Applicant: Verily Life Sciences LLC, Dallas, TX (US)

(72) Inventors: Supriyo Sinha, Menlo Park, CA (US); Kirk Gossage, Pacifica, CA (US); Dimitri Azar, Chicago, IL (US)

(73) Assignee: Verily Health Inc., Dallas, TX (US)

( * ) Notice: Subject to any disclaimer, the term of this patent is extended or adjusted under 35 U.S.C. 154(b) by 302 days.

(21) Appl. No.: 18/408,420

(22) Filed: Jan. 9, 2024

(65) Prior Publication Data

US 2024/0237894 A1    Jul. 18, 2024

Related U.S. Application Data

(60) Provisional application No. 63/479,856, filed on Jan. 13, 2023.

(51) Int. Cl.
| | |
|---|---|
| *A61B 3/11* | (2006.01) |
| *A61B 3/00* | (2006.01) |
| *A61B 90/50* | (2016.01) |

(52) U.S. Cl.
CPC ............ *A61B 3/112* (2013.01); *A61B 3/0025* (2013.01); *A61B 3/005* (2013.01); *A61B 2090/502* (2016.02)

(58) Field of Classification Search
CPC ....... A61B 3/112; A61B 3/0025; A61B 3/005; A61B 3/113; A61B 2090/502; G02B 27/0093; G02B 27/0172; G06F 3/013
See application file for complete search history.

(56) References Cited

U.S. PATENT DOCUMENTS

| | | | |
|---|---|---|---|
| 11,612,316 B2 | 3/2023 | Zidan et al. | |
| 2011/0170064 A1* | 7/2011 | Taylor | A61B 3/113 |
| | | | 351/209 |
| 2016/0262608 A1* | 9/2016 | Krueger | G16H 40/63 |
| 2018/0333092 A1 | 11/2018 | Roshan et al. | |
| 2020/0397288 A1 | 12/2020 | Zidan et al. | |

FOREIGN PATENT DOCUMENTS

| | | | |
|---|---|---|---|
| WO | 2009/109750 A1 | 9/2009 | |
| WO | WO-2017025325 A1 * | 2/2017 | ........... A61B 5/6821 |
| WO | 2023/285542 A1 | 1/2023 | |

OTHER PUBLICATIONS

WO2017025325 (Year: 2017).*
Broadway, D.C.; "How to test for a relative afferent pupillary defect (RAPD);" Community Eye Health Journal; vol. 25; Issues 79 & 80; 2012; pp. 58-59.
Yang, Y.; "Pupil Location under Mesopic, Photopic, and Pharmacologically Dilated Conditions;" Invest Ophthalmol Vis Sci. Jul. 2002; 43(7): 2508-2512; https://www.ncbi.nlm.nih.gov/pmc/articles/PMC2989408/; pp. 1-10.
International Search Report and Written Opinion received for PCT Patent Application No. PCT/US24/11139, mailed on Apr. 22, 2024, 13 pages.

* cited by examiner

*Primary Examiner* — Travis S Fissel
(74) *Attorney, Agent, or Firm* — Christensen O'Connor Johnson Kindness PLLC

(57) ABSTRACT

Virtual reality, VR, headset-based electronic systems that can be used to perform afferent pupil defect, APD, tests. The systems may improve the sensitivity, consistency, and ease of application of the APD tests. Other aspects are also described.

18 Claims, 4 Drawing Sheets

AFFERENT PUPIL DEFECT TESTING IN A VR HEADSET

CROSS-REFERENCE TO RELATED APPLICATION

This nonprovisional patent application claims the benefit of the earlier filing date of U.S. Provisional Application No. 63/479,856 filed 13 Jan. 2023, which is hereby incorporated by reference in its entirety.

FIELD

An aspect of the disclosure here relates to portable head worn equipment that can be used for detecting an afferent pupil defect of the user's eyes.

BACKGROUND

Traditionally, afferent pupil defect (APD) tests are performed by hand, by a trained eye care professional. The manual APD test can be used to detect the presence or not of an APD, but the magnitude or severity of the APD would be qualitatively judged by the practitioner. The results or sensitivity of the test thus vary by practitioner.

SUMMARY

One aspect of the disclosure here is a virtual reality, VR, headset-based electronic system that performs an afferent pupil defect, APD, test upon a user. These systems may improve the sensitivity, consistency, and ease of conducting the test in various ambient light environments, in a more efficient (less time consuming) manner. The results of the APD test may then be used by, for example, an eye care professional to diagnose a health problem with a user that might call for additional testing or a recommended treatment.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the Claims section. Such combinations may have advantages that are not recited in the above summary.

BRIEF DESCRIPTION OF THE DRAWINGS

Several aspects of the disclosure here are illustrated by way of example and not by way of limitation in the figures of the accompanying drawings in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

DETAILED DESCRIPTION

Several aspects of the disclosure with reference to the appended drawings are now explained. Whenever the shapes, relative positions and other aspects of the parts described are not explicitly defined, the scope of the invention is not limited only to the parts shown, which are meant merely for the purpose of illustration. Also, while numerous details are set forth, it is understood that some aspects of the disclosure may be practiced without these details. In other instances, well-known circuits, structures, and techniques have not been shown in detail so as not to obscure the understanding of this description.

Figure 1:
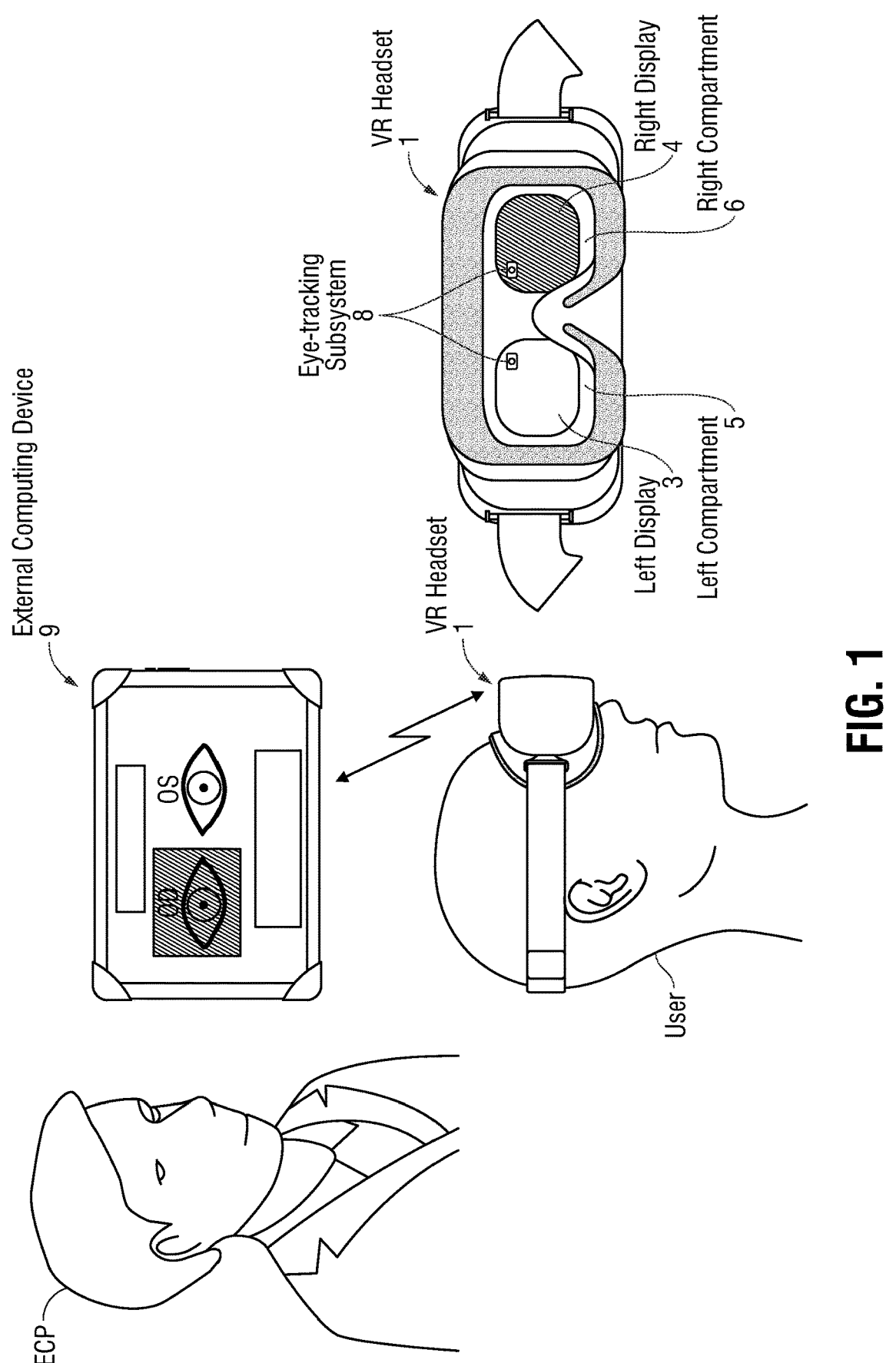
FIG. 1 is a diagram of an example virtual reality, VR, headset-based system for afferent pupil defect, APD, testing.

FIG. 1 is a diagram of an example virtual reality, VR, headset-based system that can be used for APD testing. The system is composed of a VR headset 1 which has a wired or wireless communication network interface for communicating data with an external computing device 9, e.g., a tablet computer, a laptop computer, etc. A human operator, such as an eye care professional, ECP, may interact briefly with software that is being executed by one or more microelectronic data processors (generically, "a processor") of the system to conduct the test. Once launched or initialized the software may conduct the test automatically (without input from the operator) by controlling the various electronic and optical components of the VR headset 1. The software may have components that are being executed by a processor that is in the VR headset 1, and it may have components that are executed by a processor which is part of the external computing device 9, while the VR headset 1 is fitted over a user's eyes as shown. Some of these software components may be executed either in the VR headset 1 or in the external computing device 9. The software may interact with the operator through a graphic user interface that uses a touchscreen of the external computing device 9, including presenting results of the test.

The VR headset 1 may have a form factor like goggles, as shown, that blocks all ambient lighting outside of the VR headset 1 so as to create a light controlled environment around the user's eyes (that is independent of the ambient lighting outside of the VR headset 1). The VR headset 1 may be composed of a left visible light display 3 to which a left compartment 5 is coupled that fits over the left eye of the user, and a right visible light display 4 to which a right compartment 6 is coupled that fits over the right eye of the user. The left and right compartments are configured, e.g., shaped and being opaque, so that the user cannot see the right display 4 using only their left eye, and the user cannot see the left display 3 using only their right eye (once the VR headset 1 has been fitted over the user's eyes). Also, the left and right displays need not be separate display screens, as they could instead be the left and right halves of a single display screen. The displays may be implemented using technology that provides sufficient display resolution or pixel density, e.g., liquid crystal display technology, organic light emitting diode technology, etc. Although not shown, there may also be an eyecup over each of the left and right displays that includes optics (e.g., a lens) serving to give the user the illusion that an object they see in the display (which may be displayed in 2D or in 3D) is at a greater distance than the actual distance from their eye to the display, thereby enabling more comfortable viewing. The headset might also incorporate trial lenses or some other adjustable refractive optical system to accommodate patients with different refractive errors.

The VR headset 1 also has a non-visible light-based eye tracking subsystem 8, e.g., an infrared pupil tracking subsystem, whose output eye tracking data can be interpreted by the processor for independently tracking the positions of the left and right eyes, detecting blinks, and detecting pupil size or diameter, in a way that is invisible to the user. In one aspect, the tracking subsystem is an infrared pupil tracking subsystem that produces images of pupils of the left eye and the right eye and enables a processor to record sizes of the left pupil and the right pupil over time that have a resolution of less than one millimeter.

The system has a processor that is configured by software, or instructions stored in a machine readable medium such as solid state memory, to conduct the APD test, when the headset has been fitted over the user's eyes. The term "processor" may refer to one or more microelectronic devices that are part of the external computing device 9, one or more that are within the housing of the VR headset 1, or a combination of microelectronic devices in the external computing device 9, the VR headset 1 and perhaps in another computing device that are communicating with each other through a digital communication interface. For example, the processor may be external to the VR headset 1 and receives through a wired or wireless communications network interface the tracking data from the eye tracking subsystem. The processor may be configured to signal a further display, for example the display screen of the external computing device 9, to display progress of or the results of the APD test.

The APD test may proceed as follows, referring now to the operations depicted in the flow diagram of FIG. 2. Note here that unless clearly implied by context or explicitly mentioned, the operations of a method or process need not be performed sequentially in the order shown or described, as in some cases two or more operations can overlap in time or occur in a different order. Once the headset has been fitted over the user's eyes as seen for example in FIG. 1, the method begins in operation 11 with the processor signaling the left visible light display and the right visible light display to simultaneously display a background with extremely low light, e.g., less 0.5 cd per square meter. The background may thus be dark or have no light across the entire screen of the display, e.g., obtained by signaling zero pixel intensity values across the entire screen of the display. The background may cause the pupil of a normal eye to become fully dilated, e.g., 4 to 8 mm in size.

Next, in operation 13 the processor signals only one of the left display or the right display, e.g., the left display, to display a stimulus of a predetermined brightness (e.g., a region of light that may extend across the entire screen). In other words, the other display, in this example being the right display, remains background. The stimulus may be designed to cause the pupil of a normal eye to become constricted, e.g., 2 to 4 mm in size. The stimulus may be displayed between one-half second and two seconds for example, before the display transitions back to the background or dark phase. This momentary event may also be referred to here as a flash. FIG. 1 shows an example of this where only the left eye (OS) is flashed with the stimulus.

Next, in operation 14, the processor is signaling the left visible light display and the right visible light display to simultaneously display the background. Resuming background here allows both pupils to re-dilate in preparation for the next stimulus interval. This middle background interval may for example be 3 to 7 seconds long.

Next, in operation 16, the processor is signaling only the other one of the left display or the right display (not the one in operation 13) to display the stimulus. In the example here, now the right display is showing the stimulus while the left display remains background (and no stimulus.)

In some cases, the processor then continues with operation 17 in which it signals the left display and the right display to simultaneously show the background only (no stimulus.)

During these operations 11-17 where the display transitions between dark background phase and light stimulus phase, the processor records sizes of the left pupil and the right pupil over time based on the tracking data from the eye tracking subsystem (operation 18). It may also store the recorded sizes as a data set or results of the test associated with the user. For example, the processor may be configured to display the recorded sizes of the left pupil and the right pupil over time, or the determined speeds at which the left pupil and the right pupil constrict and recover, as part of a history of afferent pupil defect testing performed on the user.

The results of the test, showing the changes in pupil size over time, synchronized with the timing of the dark and light phases, may be interpreted by the operator in diverse ways. For example, if the user has normal eyes, then both eyes should dilate during the dark background phase and then when only the left eye is flashed (in the light stimulus phase in operation 13, where only the left display transitions from low light to high light while the right display remains in low light), there should be a symmetric constriction of both the left and the right pupils. The test is normal (or no afferent pupil defect is detected) if when flashing only the right eye (operation 16) again both eyes constrict symmetrically.

Figure 3:
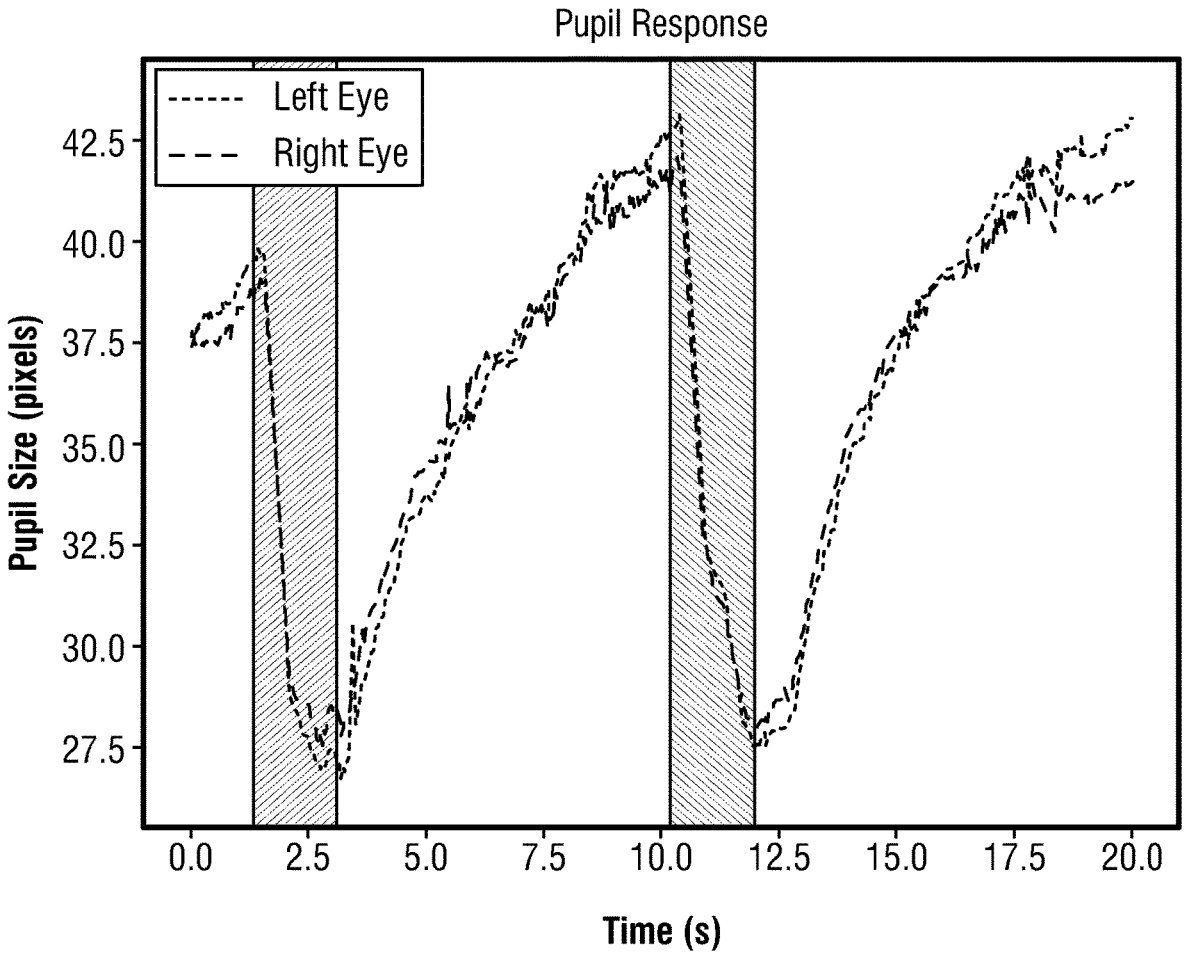
FIG. 3 illustrates an example pupil response recorded as part of the APD testing method, showing no afferent pupil response.

FIG. 3 illustrates an example of a pupil response or pupil size data set, recorded as part of the APD testing method, which may be displayed to the operator (for example on the display of the external computing device 9). The pupil size of both eyes is plotted against time, where in this example the pupil size is given in pixels which can easily be converted into distance in millimeters based on a resolution of the eye tracking subsystem (where in this example is 6.4 pixels per mm). At the end of an initial or starting background interval, the left eye is flashed around the 2.5 s mark in a first stimulus interval (operation 13), and then the right eye is flashed around the 11 s mark in a second stimulus interval (operation 16), with the middle background interval from about the 3 s mark to the 10 s mark. The background and stimulus intervals are shaded differently so as to be distinguishable in the plot, making it easy for the operator to interpret the test results. It can be seen from the plotted pupil size that in both flash intervals, both pupils constrict symmetrically. The operator may interpret this as showing no afferent pupil response. In contrast, if the pupil size data were to show that there is less pupil constriction in one eye than in the other, then the operator might interpret that as indicating an APD (due to retinal or optic nerve disease.)

Figure 2:
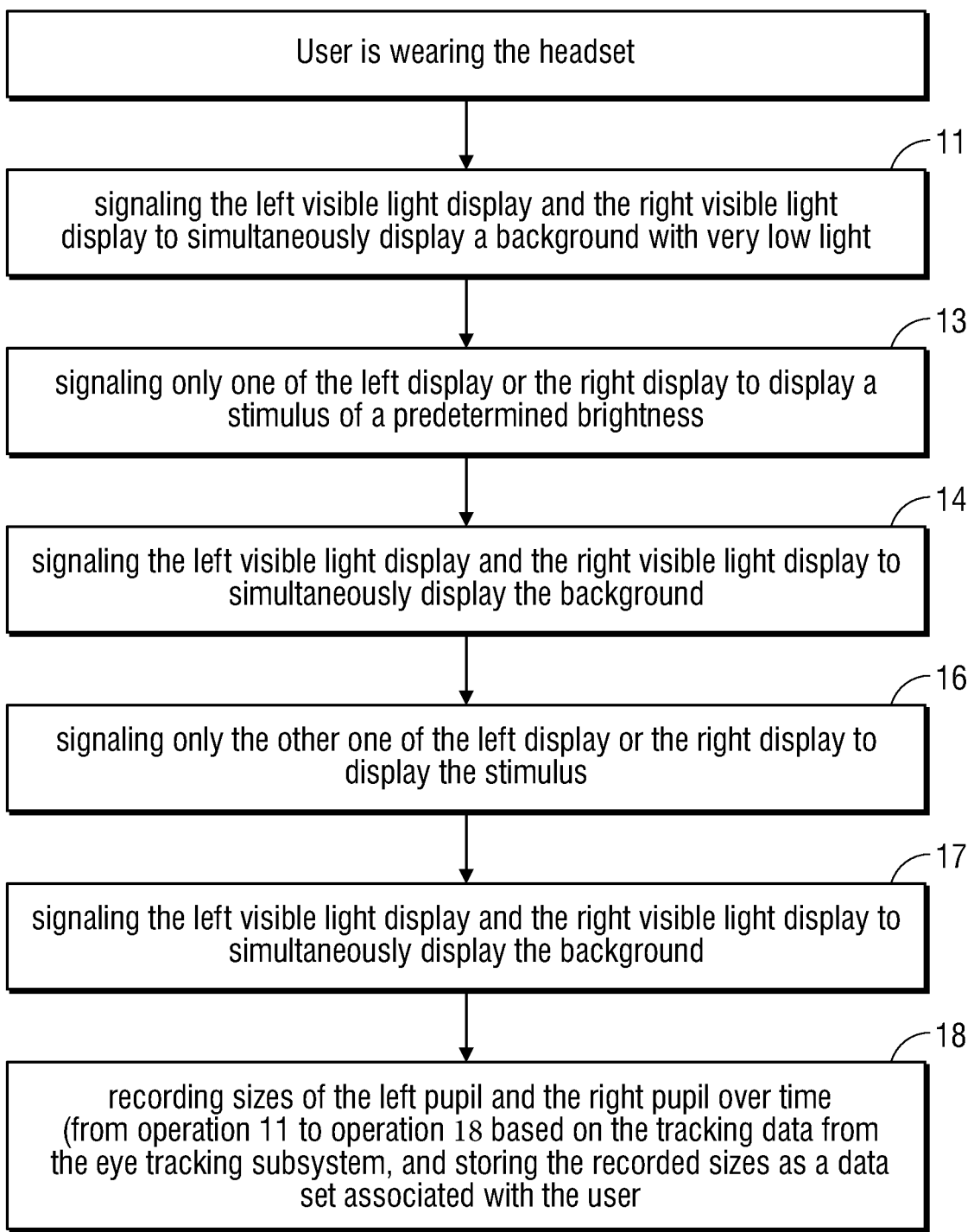
FIG. 2 is a flow diagram of a method for APD testing using the system of FIG. 1 for example.

One variation to the test in FIG. 2 is to configure the processor to omit the middle background interval, which is added in operation 14 (between operations 13 and 16). In other words, only the left eye is flashed and then immediately after that only the right eye is flashed. In another variation, either the ending background interval in operation 17 or the starting background interval in operation 11 may be omitted.

Figure 4:
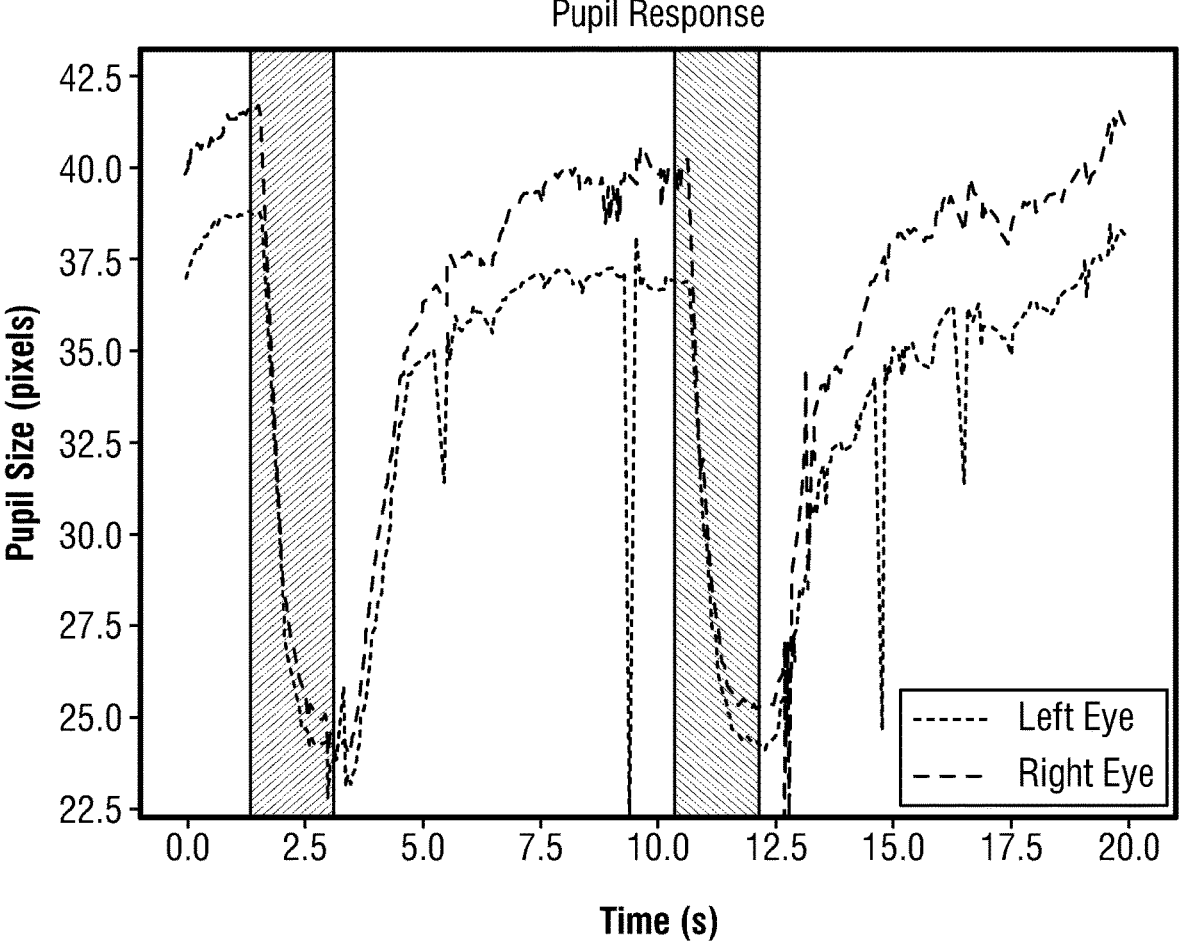
FIG. 4 illustrates an example pupil response recorded as part of the APD testing method, showing no afferent pupil response detected but subtle anisocoria detected.

The processor may be further configured to interpret the pupil size data set to flag conditions that could be interpreted by the operator as indicating anisocoria. For example, FIG. 4, illustrates an example pupil size data set (recorded as part of the APD testing method described above) showing no afferent pupil response but subtle anisocoria in the dark. The processor may be configured to mark the data set where the recorded sizes of the left pupil and the right pupil, over a same time interval of at least one second where the background is being displayed, differ by more than a threshold. During every background interval (dark phase), the processor compares the recorded left and right pupil sizes to each other and if they differ by more than the threshold, then the processor asserts a notification or flag as part of the data set indicating such a finding.

The processor may also be configured to analyze the pupil size data set and mark the data set where the left pupil and the right pupil do not constrict symmetrically, over a same time interval of for example at least one half of a second, in response to the stimulus being displayed in that time interval.

In another aspect, the processor is further configured interpret the recorded pupil sizes to determine speeds at which the left pupil and the right pupil constrict and then recover in the middle background interval and store the determined speeds as further data associated with the user.

In yet another aspect of the disclosure here, the processor may be further configured to perform the following test and interpret the resulting pupil size data set to flag conditions that could be interpreted by the operator as indicating anisocoria in the light. The test may begin with signaling both the left display and the right display to simultaneously display the stimulus for a given time interval (a stimulus or light phase). During that light phase, the processor records sizes of the left pupil and the right pupil, based on the tracking data from the eye tracking subsystem over the given time interval, and stores the recorded size as another data set associated with the user. It interprets and marks this data set whenever the recorded sizes of the left pupil and the right pupil differ by more than a threshold.

In yet another aspect, the processor is configured to signal the left display or the right display to illuminate the left eye or the right eye at a mesopic level while displaying a target stimulus (an object or symbol), and the operator may ask the user to identify the target stimulus. The mesopic level produced by the display may be in the luminance range 0.01 to 3.0 cd per square meter.

While certain aspects have been described and shown in the accompanying drawings, it is to be understood that such are merely illustrative of and not restrictive on the broad invention, and that the invention is not limited to the specific constructions and arrangements shown and described, since various other modifications may occur to those of ordinary skill in the art. The description is thus to be regarded as illustrative instead of limiting.

What is claimed is:

1. A headset-based system, the system comprising:
a headset comprising:
    a left visible light display;
    a left compartment adapted to fit over a left eye of a user and block out environment light;
    a right visible light display;
    a right compartment adapted to fit over a right eye of the user and block out the environment light, wherein the left and right compartments are configured so that when the headset has been fitted over the user's eyes i) the user cannot see the right display using only their left eye and ii) the user cannot see the left display using only their right eye;

light sensors disposed inside the left and right compartments to detect levels of the environment light that leaks into the left compartment or the right compartment; and
a non-visible light-based eye tracking subsystem that produces tracking data for the left eye and for the right eye; and
a processor configured to, when the headset has been fitted over the user's eyes;
    i) signal the left display and the right light display to simultaneously display a background with a first level of brightness, and then
    ii) signal only one of the left display or the right display to display a stimulus of a predetermined brightness that is brighter than the first level of brightness, and then
    iii) signal only the other one of the left display or the right display to display the stimulus, and
    iv) during i)-iii) record sizes of a left pupil and a right pupil over time based on the tracking data from the eye tracking subsystem and store the recorded sizes as a data set associated with the user,
wherein the processor is further configured to record the levels of the environment light for the left compartment and the right compartment representing an external light contribution while the headset is fitted over the right and left eyes of the user.

2. The system of claim 1 wherein the processor is further configured to add a middle background interval, by signaling the left display and the right display to simultaneously display the background after ii) and before iii).

3. The system of claim 2 wherein the processor is further configured to interpret the recorded sizes to determine speeds at which the left pupil and the right pupil constrict and then recover in the middle background interval and store the determined speeds as further data associated with the user.

4. The system of claim 1 wherein the processor is further configured to:
mark the data set where the recorded sizes of the left pupil and the right pupil, over a same time interval of at least one second where the background is being displayed, differ by more than a threshold.

5. The system of claim 1 wherein the processor is further configured to:
mark the data set where the left pupil and the right pupil do not constrict symmetrically, over a same time interval of at least one half of a second, in response to the stimulus being displayed.

6. The system of claim 1 wherein the processor is further configured to:
signal the left display and the right display to simultaneously display the stimulus for a given time interval;
record sizes of the left pupil and the right pupil, based on the tracking data from the eye tracking subsystem over the given time interval, and store the recorded size as another data set associated with the user; and
mark the another data set where the recorded sizes of the left pupil and the right pupil differ by more than a threshold.

7. The system of claim 1 wherein the processor is further configured to signal the left display or the right display to illuminate the left eye or the right eye at a mesopic level while displaying a target stimulus.

8. The system of claim 3 wherein the processor is configured to display the recorded sizes of the left pupil and the right pupil over time, or the determined speeds at which the left pupil and the right pupil constrict and recover, as part of a history of afferent pupil defect testing performed on the user.

9. The system of claim 1 wherein the background is dark or no light.

10. The system of claim 1 wherein the stimulus is a light region.

11. The system of claim 1 wherein the stimulus is displayed between one-half second and two seconds.

12. The system of claim 1 wherein the recorded sizes of the left pupil and the right pupil over time have a resolution of less than one millimeter.

13. The system of claim 1 wherein the processor is external to the headset, and the headset comprises a wired or wireless communications network interface through which the tracking data from the eye tracking subsystem is sent to the processor.

14. The system of claim 1 wherein the eye tracking subsystem is an infrared pupil tracking subsystem that produces images of pupils of the left eye and the right eye.

15. A method for pupil defect testing comprising:

i) signaling a left display and a right light display of a headset to simultaneously display a dark background, and then ii) signaling only one of the left display or the right display to display a light stimulus, and then iii) signaling only the other one of the left display or the right display to display the light stimulus, v) during i)-iii) record sizes of a left pupil and a right pupil of a user of the headset over time, based on tracking data from an eye tracking subsystem in the headset, and store the recorded sizes as a data set associated with the user, and vi) marking the data set where the recorded sizes of the left pupil and the right pupil, over a same time interval of at least one second where the background is being displayed, differ by more than a threshold.

16. The method of claim 15 further comprising adding a middle background interval by signaling the left display and the right display to simultaneously display the dark background after ii) and before iii).

17. The method of claim 15 further comprising marking the data set where the left pupil and the right pupil do not constrict symmetrically, over a same time interval of at least one half of a second, in response to the stimulus being displayed.

18. The method of claim 15 further comprising:

signaling the left display and the right display to simultaneously display the stimulus for a given time interval;

recording sizes of the left pupil and the right pupil, based on the tracking data from the eye tracking subsystem over the given time interval, and store the recorded size as another data set associated with the user; and mark the another data set where the recorded sizes of the left pupil and the right pupil differ by more than a threshold.

* * * * *